United States Patent [19]

Chynoweth et al.

[11] 4,334,026

[45] Jun. 8, 1982

[54] HYBRID BIO-THERMAL LIQUEFACTION

[75] Inventors: David P. Chynoweth, St. Charles; Paul B. Tarman, Elmhurst, both of Ill.

[73] Assignee: Institute of Gas Technology, Chicago, Ill.

[21] Appl. No.: 186,248

[22] Filed: Sep. 11, 1980

Related U.S. Application Data

[63] Continuation-in-part of Ser. No. 113,242, Jan. 18, 1980, Pat. No. 4,289,625.

[51] Int. Cl.$^3$ .............................................. C12P 7/08
[52] U.S. Cl. ................................. 435/163; 435/165; 127/37; 210/610
[58] Field of Search ................ 210/610, 611, 768–771, 210/774; 435/161–165; 127/36, 37

[56] References Cited

U.S. PATENT DOCUMENTS

| | | | |
|---|---|---|---|
| 2,312,196 | 2/1943 | St.-Leger | 435/165 |
| 3,728,279 | 4/1973 | Salomone | 210/611 X |
| 4,093,516 | 6/1978 | Lang | 435/165 |
| 4,094,740 | 6/1978 | Lang | 435/165 X |
| 4,200,523 | 4/1980 | Balmat | 210/611 |

*Primary Examiner*—Thomas G. Wyse

*Attorney, Agent, or Firm*—Thomas W. Speckman

[57] ABSTRACT

A hybrid bio-thermal liquefaction process for improved carbonaceous liquefaction to produce alcohol containing fuels wherein an organic carbonaceous feed is subjected to active fermentation producing alcohol containing liquid fuel product and fermentation residue, the fermentation residue being introduced into a thermochemical converter and at least a substantial portion of the organic carbon component of the residue converted under elevated temperature conditions producing thermochemical converter products and thermochemical residue with a portion of at least one of the thermochemical products or their derivatives, or thermochemical residue being passed to the fermentation reactor. The process provides high overall process energy efficiencies and utilizes the total agricultural biomass crop thereby greatly reducing waste disposal problems. The alcohol content (ethanolmethanol) of the liquid fuels produced can be increased by utilization of embodiments of the process emphasizing thermochemical gas production followed by catalytic synthesis while the fuel oil and gasoline content of the liquid fuels produced can be increased by embodiments of the process emphasizing thermochemical liquefaction.

33 Claims, 2 Drawing Figures

HYBRID BIO-THERMAL LIQUEFACTION

CROSS REFERENCE TO RELATED APPLICATION

This application is a continuation-in-part of our earlier filed application, Ser. No. 113,242, filed Jan. 18, 1980, entitled HYBRID BIO-THERMAL GASIFICATION, U.S. Pat. No. 4,289,625.

BACKGROUND OF THE INVENTION

1. Field of the Invention

Liquid fuel production by fermentation of cellulosic materials has been recognized in the production of ethanol. In recent times, the worldwide energy shortage has furthered consideration and improvement of non-fossil sources of energy. Biological materials and organic wastes, represent a large renewable potential energy resource. This invention relates to improved liquefaction from organic materials by hybrid biological-thermal liquefaction to provide substantially increased conversion to alcohol containing fuels of the organic component of the feed material, including terrestrial and aquatic energy crops, organic wastes and peat. The process of this invention provides fermentation of an organic carbonaceous feed producing alcohol containing liquid fuel followed by thermochemical conversion of the fermentation residue and plant portions not used for fermentation, the thermochemical conversion providing product gas or liquid, a portion of which or a derivative thereof, such as ammonia or hydrogen, may be supplied to the fermentation reactor for improved fermentation. Product gas from thermochemical conversion may also be converted to liquid fuels by catalytic synthesis or product liquids from thermochemical liquefaction may be separated or upgraded to provide alcohol containing liquid fuel. The thermal residue from such gasification or liquefaction may be recycled to the fermentation reactor to provide phosphorus and other inorganic nutrients. The hybrid bio-thermal liquefaction process of this invention broadens the range of organic feeds suitable for conversion, provides higher liquid fuel production per pound of organic feed, and substantially reduces the quantity of residue from the process over currently known processes. The hybrid bio-thermal liquefaction process of this invention may additionally provide medium Btu fuel gas, ammonia and hydrogen containing gas for a variety of uses. Thermal energy from the thermal conversion may advantageously be used in other steps of the process, such as distillation, pretreatment, fermentation or dewatering, providing an overall high energy efficiency.

DESCRIPTION OF THE PRIOR ART

The production of ethanol and other liquid fuels by bioconversion of cellulose of various agricultural materials and organic wastes has been known. There have been continuous efforts to improve the liquid fuel and particularly the ethanol yield resulting from bioconversion of cellulose. Ethanol production using cell recycle and vacuum fermentation processes involving continuous processes utilizing molasses has been described by Gerald R. Cyseurski and Charles R. Wilke, Process Design and Economic Studies of Alternative Fermentation Methods for the Production of Ethanol, Biotechnology and Bioengineering, Vol. XX, pp. 1421-1444, John Wiley and Sons, Inc. (1978). Use of agricultural residues and whole tree materials for ethanol fermentation production of ethanol has been described by Charles R. Wilke, Harvey W. Blanch, Aldo F. Sciomanna, Steven L. Rosenberg, S. Kishen Tangnu and Ray P. Freitas, Process Development Studies on the Bioconversion of Cellulose and Production of Ethanol, Proceedings of 3rd Annual Biomass Energy Systems Conference, Solar Energy Research Institute, Department of Energy, Golden, Colo., pp. 79-84 (1979) and butanol liquid fuels by fermentation has been described by E. Kendall Pye and Arthur E. Humphrey, Production of Liquid Fuels from Cellulosic Biomass, Proceedings of 3rd Annual Biomass Energy Systems Conference, ibid., pp. 69-75. The direct anaerobic production of ethanol from cellulosic biomass has been described by Charles L. Cooney, Daniel I. C. Wang, Sy-dar Wang, Jennifer Gorden and Margarita Jiminez, Simultaneous Cellulose Hydrolysis and Ethanol Production by a Cellulolyltic Anaerobic Bacterium, Biotechnology and Bioengineering Symp. No. 8, pp. 103-114, John Wiley and Sons, Inc. (1978).

The prior art recognizes the desirability of utilization of various biomass materials for biological conversion to produce usable liquid fuels, especially due to the high water content of such biomass materials making them unsuitable for other modes of conversion. However, the overall conversions and energy balances have not been as efficient as desired. Current reported processes for grain conversion to ethanol have overall process energy efficiencies of 26-28 percent. There has also been recognition of the undesired large amounts of fermentation residues. The prior art, while recognizing the desirability to increase liquid fuel production by fermentation of biomass, does not suggest the combination of biological fermentation and thermochemical conversion to utilize substantially all of the organic carbonaceous material in the organic feed together with beneficiation of the fermentation culture by the thermal conversion residue or products. Feed residues, such as corn stover, bagasse, may be used directly to produce additional liquid-fuels and to supply thermal energy to the process and provide high overall energy efficiencies.

SUMMARY OF THE INVENTION

The process of this invention provides a hybrid biological-thermal process for improved carbonaceous liquefaction comprising adding organic carbonaceous feed to a fermentation reactor, fermenting the organic carbonaceous feed under thermophilic or mesophilic conditions in an active alcohol producing liquid culture, separating alcohol containing liquid fuel product and fermentation residue and introducing the fermentation residue into a thermochemical converter which may be a thermal gasifier or thermal liquefier, or both, wherein at least a substantial portion of the carbonaceous material in the fermentation residue is converted under elevated temperature conditions thereby producing thermal conversion products used directly or converted by catalytic synthesis to alcohol containing liquid fuel and thermal residue. At least a portion of the thermal conversion products or their derivatives may be passed to the fermentation reactor to beneficiate the fermentation process. In one embodiment, at least a portion of the thermal residue may be returned to the fermentation reactor to provide inorganic nutrients for the fermentation. In another embodiment, ammonia may be added to the fermentation reactor, the ammonia being a thermal converter product or produced from product gases of the thermal converter. The process of this invention provides for the catalytic synthesis of alcohols from the gases produced by thermochemical gasification or liquefaction of the fermentation residue from the fermentation reactor providing higher alcohol production per unit of feed than conventional fermentation processes. In another embodiment, the low BTU gases produced by thermochemical gasification or thermochemical liquefaction of the fermentation residue may be used as fuel gas.

It is an object of this invention to provide a process for high conversion of carbonaceous material in organic carbonaceous feed stocks to liquid fuel products thereby greatly reducing waste disposal problems associated with conventional biomass fermentation processes.

It is another object of this invention to provide a liquefaction process applicable to a wider variety of biological feed stocks than presently available processes.

It is a further object of this invention to provide a combined biological fermentation and thermochemical conversion process for high efficiency production of liquid fuels.

It is still another object of this invention to provide a hybrid biological-thermochemical process for liquid fuel production which efficiently converts feed stocks having high water content, greater than 50 percent.

It is an object of this invention to provide a biological-thermochemical process for production of liquid fuel utilizing the entire plant material including feed residues to improve the overall energy balance of the process.

It is yet another object of this invention to provide a hybrid biological-thermochemical carbonaceous liquefaction process requiring less external nutrient feeding due to nutrient recycle of thermal residue to the fermentation reactor.

It is a further object of this invention to provide a liquefaction process for production of alcohol containing liquid fuels from hydrocarbonaceous feed materials and having high thermal efficiency.

BRIEF DESCRIPTION OF THE DRAWINGS

Other objects and advantages of this invention will be apparent by reading of the further description of the preferred embodiments and by reference to the drawings setting forth preferred embodiments wherein.

DESCRIPTION OF PREFERRED EMBODIMENTS

Figure 1:
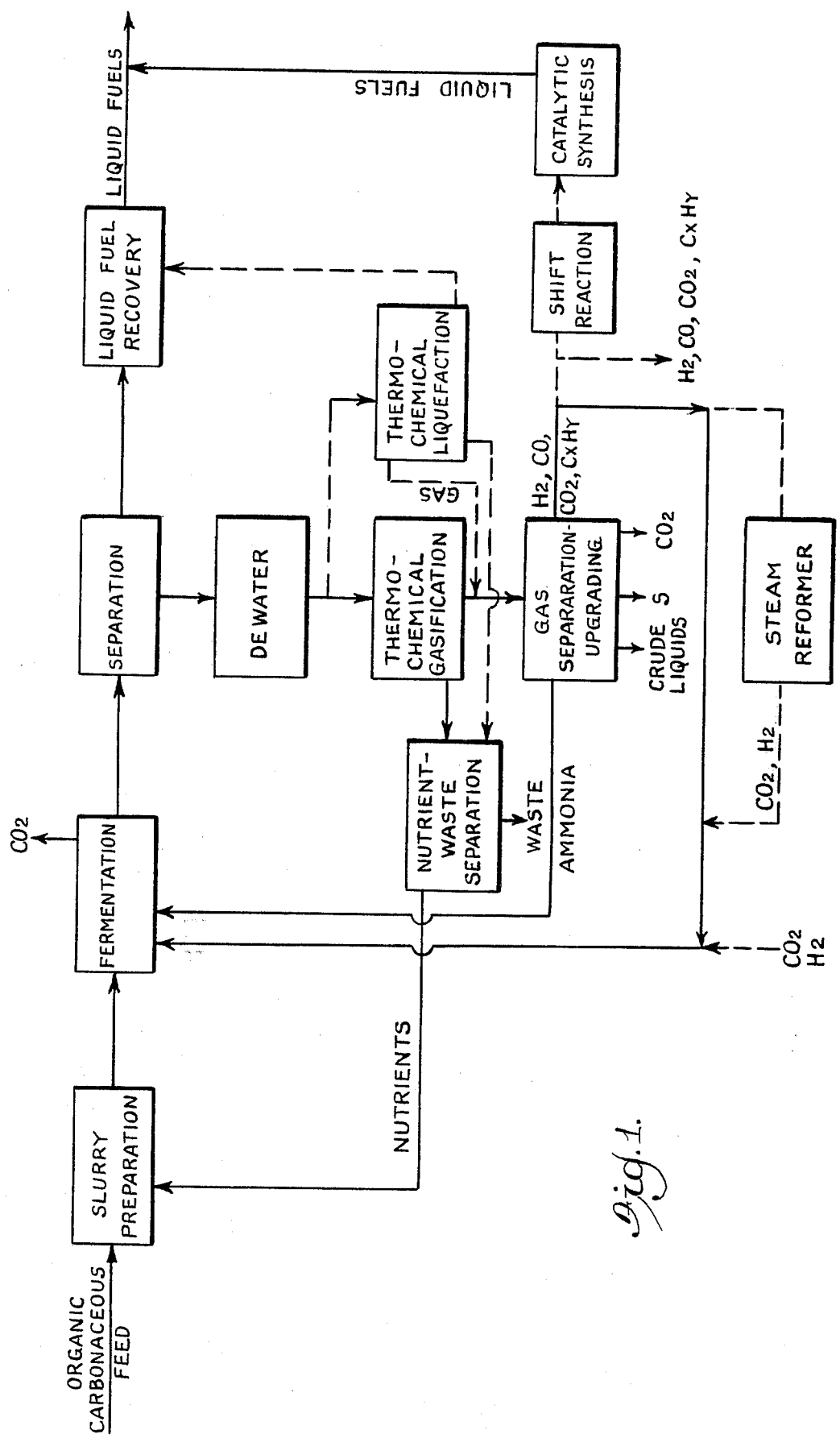
FIG. 1 is a simplified schematic diagram showing the relationship of basic steps of the hybrid bio-thermal process of this invention.

The term "organic carbonaceous feed" materials as used in this description and the appended claims includes plant material which may be of terrestrial or aquatic origin, peat and organic waste which includes all types of organic refuse including sewage sludge, animal waste, municipal waste, industrial waste, forestry waste, agricultural waste, and the like. The term "organic carbonaceous feed" materials includes biological feeds, biological digestion or fermentation residues and thermochemical gasification and liquefaction residues.

Plant material may include any of the organisms of the kingdom of Plantae which typically have cell walls composed of cellulose in large part and have nutritive systems in which carbohydrates are formed photosynthetically. The plant material useful in this invention is fresh harvested or stored plant material, which is usually grown on farms for this purpose, and is untreated chemically or physically, except for size reduction. Terrestrial plants include warm season grasses, such as Bermuda grass and Elephant grass; cool season grasses, such as Kentucky Blue grass and Merion Blue grass; reedy plants, such as Bamboo, rice, cattails; heraceous plants, such as Kudzu and maze; deciduous trees, such as eucalyptus and poplar; and coniferous trees, such as white and red pines. Exemplary aquatic plants include water hyacinth, duck weed, algae, sea kelp and sargassum.

Bioconversion of cellulose of organic waste such as sewage sludge, animal waste, municipal waste and industrial waste to alcohols by fermentation is suitable for the process of this invention. Treatment of municipal solid waste and industrial solid waste for removal of undesired material such as glass, metals, plastics, stones, and the like, is well known to the art. Forestry waste and agricultural waste includes portions of plants after some physical or chemical treatment, for example, stumps from logging, sawdust, wood chips, corn stalks, corncob and bagasse.

The fermentation of organic carbonaceous feed according to this invention may be carried out under conditions which are presently known or become available to the art. Fermentation may be carried out at temperatures of about 10° to 65° C., generally at about 20° to 40° C.; retention times in excess of about ½ day and usually about ½ to 8 days; and loading rates; pretreatment of feed; fermentation reactor mixing, recycling, batch and continuous processes as known to the art for fermentation and pointed out more particularly in the references identified. Pretreatment of the feed by methods such as enzymatic or acid hydrolysis may be necessary to produce sugars for fermentation. Many such pretreatments have been developed as described by M. C. Flickinger, Current Biological Research in the Conversion of Cellulosic Carbohydrates into Liquid Fuels, Biotechnology and Bioengineering, Vol. 22, Suppl. 1, pp. 27–48 (1980). The fermentation of the sugars to alcohols is well developed in industry and described in the literature Annual Report of Fermentation Processes, D. Purlman and G. T. Tsao, Academic Press, New York, N.Y. (1978). Shorter retention times than the preferred times set forth above may be used in the present invention under conditions where fermentation is accelerated by the process.

Any active alcohol producing fermentation system may be used. Alcohol producing fermentation systems utilizing *Saccharomyces cerevisiae*, standard yeast fermentation, *C. acetobutylicum*, and *Cl. thermosacchorolyticum* are suitable. Simultaneous hydrolysis/fermentation using Thermoactinomyces and the anaerobic bacterium *C. thermocellum* may be used as suggested by the Pye et al article referred to above. A review of fermentation is set forth in the Annular Report of Fermentation Processes, ibid., the contents of which is incorporated in its entirety herein by reference. Nutritional balance and pH adjustments may be made to the fermentation system as is known to the art to optimize ethanol production from the culture used.

Referring to the figures, the organic carbonaceous feed may be ground and mixed with water and nutrients, which may be derived primarily from process streams, prior to introduction into biological fermentation reactor 11. The organic feed may be deficient in inorganic and organic nutrients which may be added to the fermentation reactor or to the feed preparation means 95 or pretreatment means 96 and may at least in part be derived from the thermochemical residue, the thermochemical gasification or liquefaction products or their derivatives and dewatering prior to thermochemical conversion, thus, substantially broadening the suitable biological feeds and reducing requirements for addition of nutrients to the overall process. Inorganic nutrients, such as phosphorus, are derived principally from thermochemical residue and ammonia may be derived by recovery from gases produced by thermochemical gasification. Liquids and nutrients may be derived from dewatering of biological residue of the fermentation reactor and recycled to the fermentation reactor. Thus, the process may be readily adjusted with respect to nutrients and chemical deficiencies of biological or organic waste feeds by internal adjustments thereby alleviating the requirement of addition of chemicals to the overall process, especially on a continual basis during fermentation.

The water content of the biological feed is not important and may be high, more than 50 percent. One of the features contributing to the high overall energy efficiency of this process is the availability of thermal energy recovered from the thermal conversion step for various other process steps including pretreatment, fermentation, dewatering and distillation.

Slurry preparation including grinding feed to desired size and mixing takes place in slurry preparation means 95 by methods well known to the art. Pretreatment means 96 may provide hydrolysis of the organic feed material prior to fermentation as known to the art, for example, acid hydrolysis using sulfuric or hydrochloric acid or enzymatic hydrolysis. Other pre-fermentor requirements such as sterilization, pasteurization, yeast or other microbial preparation may be carried out in pretreatment means 96.

Fermentation reactor 11 may be of any configuration suitable for fermenting the organic carbonaceous feed under alcohol producing conditions in an active liquid culture and may comprise multiple stage or continuous fermentors with the supernatant from a sedimentation stage being recycled to the feed preparation means. As shown in the figures, gasification products from thermochemical gasifier 30 and/or thermochemical liquefier 35 which may contain hydrogen, lower hydrocarbons, carbon dioxide, and carbon monoxide may be provided to fermentation reactor 11. The hydrogen or carbon dioxide supplied to fermentation reactor 11 may be increased by a steam reformer used in conjunction with a shift reactor to produce hydrogen and carbon dioxide shown in FIG. 2 as steam reformer means 36 and/or adding hydrogen and/or carbon dioxide to the gas feed stream to fermentation reactor 11. The hydrogen beneficiates fermentation while the carbon dioxide acts primarily as a pH buffer. Fermenting of organic carbonaceous feed under alcohol producing conditions is beneficiated by addition of hydrogen, carbon dioxide or mixtures thereof, which may be derived from sources outside of the process or process sources as described. Carbon dioxide formed by the fermentation reaction beyond that desired for pH buffer action may be vented from the fermentation reactor 11.

Figure 2:
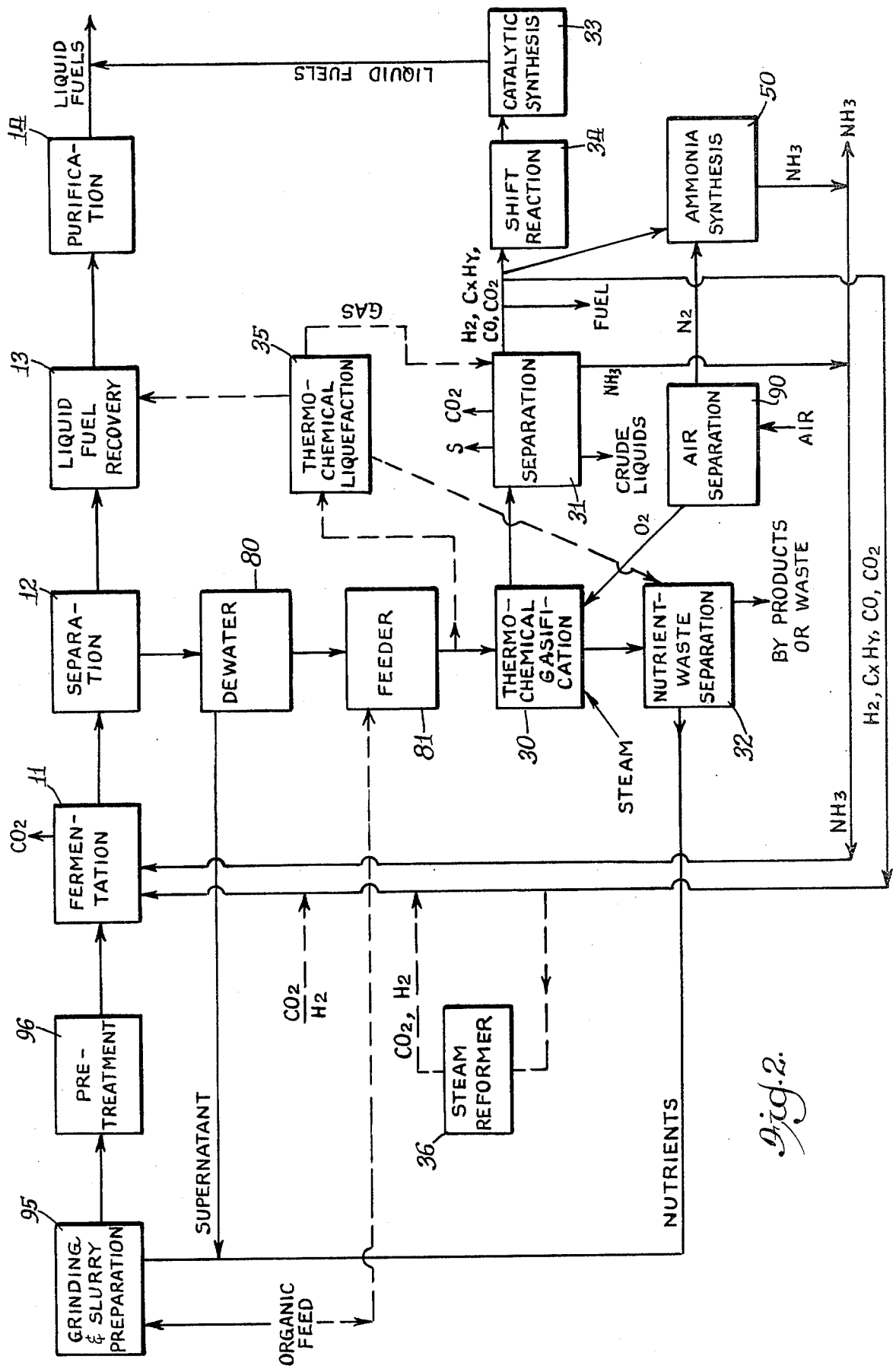
FIG. 2 is a schematic process flow diagram showing one preferred embodiment of this invention.

Ammonia for beneficiation of the active fermentation volume and pH control may be derived directly from products of thermochemical gasifier 30 and/or thermochemical liquefier 35 by separation means 31 shown in FIG. 2 and may be added to fermentor 11 or slurry preparation means 95. Suitable separation means 31 and purification and carbon dioxide and sulfur recovery processes include acid gas removal processes as described in Gas Purification, Arthur Kohl and Fred Riesenfeld, second edition, Gulf Publishing Company Book Publishing Division, Houston, Tex., (1974). When excess ammonia is available from the thermochemical converter products, it may be withdrawn from the process as shown in FIG. 2. When insufficient ammonia is available from gasifier products, it may be synthesized as shown in FIG. 2 by ammonia synthesis means 50 using nitrogen from air separation means 90, and product gases from thermal gasifier 30. Ammonia synthesis may be performed by known processes, such as Kellogg ammonia synthesis processes. Air separation processes, such as Linde processes, operating at low temperatures are suitable to provide nitrogen for ammonia synthesis and oxygen for thermochemical gasification.

At least a portion of produced gases from thermochemical gasifier 30 and/or thermochemical liquefier 35 or their derivatives may be fed to fermentation reactor 11 or ammonia synthesis means 50 or may be withdrawn from the process system for use directly as medium Btu fuel gas or may be converted by catalytic synthesis means 33 to alcohol containing liquid fuels by methods known to the art to provide additional liquid fuel output. Suitable means for catalytic synthesis of liquid fuel comprising primarily methanol from the thermal converter product gases, primarily $H_2$, $C_xH_y$, CO and $CO_2$, include those processes described in Kirk-Othmer's Encyclopedia of Chemical Technology, Second Edition, Vol. 13, pp. 370-398, Interscience Publishers, Div. of John Wiley and Sons, Inc., New York City (1967). It is desirable to remove deleterious aromatics or higher hydrocarbons and sulfur containing compounds from such product gases as shown by separation means 31. Suitable means for gas separations and purifications are reviewed in Gas Purifications, Arthur Kohl and Red Riesenfield, Second Edition, Gulf Publishing Company, Houston, Tex. (1974).

Biological residues from fermentation reactor 11 are separated from alcohol containing liquid fuels by separation means 12 which may be any suitable liquid-solid separator, such as settling or centrifugation. The alcohol containing liquid fuels are passed to liquid fuel recovery means 13 such as distillation or any other alcohol separation and purification means 14 for desired upgrading to provide liquid fuels containing predominately lower alcohols, ethanol and/or methanol.

The fermentation residues from separation means 12 are preferably dewatered by dewatering means 80 to a water content of less than about 75-80 weight percent, preferably less than about 50 weight percent and transferred to a thermochemical converter which may be thermochemical gasifier 30 or thermochemical liquefier 35 through suitable feeder means 81. Dewatering may be accomplished by filter presses or fixed bed roller processes as known in the art. The supernatant from the dewatering process may be used for feed slurry dilution as needed, thus retaining nutrients within the process. Fresh organic feed or feed residues, such as corn stover or bagasse, may also be provided to feeder 81 for introduction into thermochemical conversion means 30 or 35.

The thermochemical conversion means may be any suitable thermochemical means for conversion of organic carbon in the fermentation residue or in added organic feed or feed residues to liquid or gaseous hydrocarbons which can be converted to alcohol containing liquid fuels to increase the overall process efficiency of liquid fuel production and provide byproducts and nutrients useful for return to beneficiate fermentation. As shown in the figures, the thermochemical conversion may be provided by thermochemical gasification or thermochemical liquefaction. The thermochemical conversion converts a substantial portion, more than 50 percent, of the organic carbon in the fermentation residue to useful gaseous or liquid product.

Thermochemical gasifier 30 is operated under elevated temperature conditions to gasify a substantial portion of the biological residues, usually at temperatures of about 1200° to about 1800° F. Thermal energy for the thermochemical gasifier may be obtained by utilization of fresh organic feed and product gases of the thermochemical gasifier. The thermochemical gasification may be carried out in a single or multiple stage gasifier under conditions of pressure and residence time to gasify a substantial portion of the organic carbonaceous material in the biological residue, greater than 50 weight percent and preferably greater than 75 weight percent. It is preferred that the thermochemical gasifier be operated under pressure from atmospheric up to about 1000 psig. Moving bed or fluidized bed gasifiers are also suitable as will be apparent to those skilled in the art. Generally, residence times in the thermochemical gasifier in the order of about 3 to 60 minutes are suitable. The waste portion of the thermal residue from thermochemical gasifier 30 represents a substantially lessened disposal problem than does the biological residue from fermentation reactor 11 which has created disposal problems with prior processes. The nutrients for recycle to fermentor 11 may be separated from byproducts or waste in separator means 32. Suitable thermochemical gasifiers include those such as described in the publication "Status of the Peat Gas Process", D. Punwani, paper at Tenth Synthetic Pipeline Gas Symposium, Chicago, Ill., October 1979, and in the publication U-GAS TECHNICAL STATUS, J. G. Patel, Symposium on Advances in Coal Utilization Technology, Louisville, Kentucky, May 1979, which are incorporated herein by reference in their entireties.

Thermochemical liquefier 35 includes any suitable liquefaction technique which under thermochemical action converts organic feedstocks to useful liquid fuels, such as pyrolysis conducted in the absence of $O_2$ and steam producing gas products of the same type as produced by thermochemical gasification (CO, $H_2$, $CO_2$ and $C_xH_y$ wherein x is a number of 1 to 4 and y is a number corresponding to the produced alkane or alkene, predominately producing $CH_4$) and liquid fuels comprising lower alcohols, fuel oils and gasoline. Any suitable liquefaction process producing liquid fuels may be used such as flash pyrolysis as described in Environmental Control Technology for Biomass Flash Pyrolysis, J. B. L. Harkness, R. D. Doctor and W. H. Seward, Symposium Papers, Energy from Biomass and Wastes IV, Lake Buena Vista, Fla., Jan. 21, 1980, pp. 617-643, incorporated herein by reference in its entirety.

The liquid fuels produced by the process of this invention comprise lower alcohol containing liquid fuel comprising ethanol produced by fermentation and methanol produced from one portion of the product gas of thermochemical conversion of the fermentation residue and plant portions relatively recalcitrant to fermentation. The second portion of the product gas and direct thermal transfer from the thermochemical converter may provide all of the process thermal energy requirements. It is seen that the alcohol content (ethanolmethanol) of the liquid fuels produced can be increased by the embodiments of the process emphasizing thermochemical gas production followed by catalytic synthesis, while the fuel oil and gasoline content of the liquid fuels produced can be increased by the embodiments of the process emphasizing thermochemical liquefaction. By utilizing the entire organic carbonaceous plant material, the most readily fermentable portions for fermentation and the remainder for thermochemical gasification or liquefaction with produced gases being used for process energy requirements, overall process energy efficiencies of over about 50 percent and preferably over about 60 percent are obtainable.

The following specific example of one preferred embodiment of the process of this invention is set forth for illustration and should not be considered to limit the invention.

EXAMPLE

Total corn crop is utilized according to the process as outlined in FIG. 2 and more fully described below to produce mixed ethanolmethanol containing liquid fuel.

100,000 pounds (dry weight) of corn kernels (62% starch) are stripped from the cob, milled, slurried and subjected to standard amylase pretreatment hydrolysis. The pretreated corn kernel slurry is introduced into a batch fermentor maintained with active yeast Saccharomyces cerevisiae for a 3 day fermentation time at pH of about 4.5 and a temperature of 30° C. The fermentation vessel contents are then subjected to centrifugation separation and the supernatant is subjected to refining distillation and benzene distillation producing 27,900 pounds ethanol product.

The fermentation residue is subjected to gravity settling, centrifugation and vacuum filtration producing 4000 pounds of solids and 4000 pounds of water following dewatering. 100,000 pounds of the corn residue, comprising cobs and stover containing 50 percent water are mixed with the 8000 pounds dewatered fermentor effluent and introduced into a single stage steam-air/$O_2$ thermochemical gasifier maintained at 1700° F. and 550 psi producing mixed synthesis gas product ($CO_2$, CO, $CH_4$, $H_2$). 64 percent of the gas produced and direct thermal transfer from the thermochemical gasifier is used to provide all process energy requirements and 36 percent is available for catalytic synthesis to liquid fuels. The gases for catalytic synthesis are subjected to a CO+water shift reaction and catalytic methanol synthesis producing 16,900 pounds of methanol.

The process as described in this specific example provides an overall energy efficiency of 65 percent while producing 44,800 pounds of mixed ethanol (27,900 pounds)-methanol (16,900 pounds) liquid fuel from 200,000 pounds of total corn crop, 100,000 pounds kernels and 100,000 pounds corn residue including cobs and stover. Current reported processes for grain conversion to ethanol have overall process energy efficiencies of 26-28 percent.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A hybrid bio-thermal liquefaction process for improved carbonaceous liquefaction to produce alcohol containing liquid fuels comprising: adding organic carbonaceous feed to a fermentation reactor; fermenting said organic carbonaceous feed under alcohol producing conditions in an active alcohol producing biological liquid culture; separating alcohol containing liquid fuel product and fermentation residue and dewatering and introducing said fermentation residue into a thermochemical converter; thermochemically converting at least a substantial portion of the organic carbon component of said fermentation residue under elevated temperature conditions producing thermochemical converter products and thermochemical residue, a portion of at least one of said thermochemical products or their derivatives or thermochemical residue being passed to said fermentation reactor.

2. The process of claim 1 wherein said portion of thermochemical products comprises hydrogen containing gas passed to said fermentation reactor.

3. The process of claim 1 wherein said portion of said thermochemical products or their derivatives comprises ammonia passed to said fermentation reactor.

4. The process of claim 1 wherein thermochemical residue comprising nutrients for said active fermentation culture are passed to said fermentation reactor.

5. The process of claim 1 wherein said thermochemical converting comprises gasification.

6. The process of claim 5 wherein said gasification is conducted at temperatures about 1200° to 1800° F. in the presence of steam and oxygen containing gas.

7. The process of claim 5 wherein said thermochemical converter products comprise gas comprising hydrogen, carbon monoxide, carbon dioxide and low molecular weight hydrocarbon gases.

8. The process of claim 7 wherein at least a portion of said product gas is utilized to provide thermal energy for said process.

9. The process of claim 7 wherein at least a portion of said product gas is fed to an ammonia synthesis means to produce ammonia to pass to said fermentation reactor.

10. The process of claim 7 wherein at least a portion of said product gas is fed to a shift reaction means and catalytic synthesis means to produce additional alcohol containing liquid fuels.

11. The process of claim 1 wherein said thermochemical converting comprises thermochemical liquefaction.

12. The process of claim 11 wherein said thermochemical liquefaction products comprise liquid fuels comprising lower alcohols, fuel oils and gasoline.

13. The process of claim 11 wherein said thermochemical liquefaction products comprise gas comprising hydrogen, carbon monoxide, carbon dioxide and low molecular weight hydrocarbon gases.

14. The process of claim 13 wherein at least a portion of said product gas is utilized to provide thermal energy for said process.

15. The process of claim 13 wherein at least a portion of said product gas is fed to an ammonia synthesis means to produce ammonia to pass to said fermentation reactor.

16. The process of claim 13 wherein at least a portion of said product gas is fed to a shift reaction means and catalytic synthesis means to produce additional alcohol containing liquid fuels.

17. The process of claim 11 wherein said thermochemical liquefaction comprises flash pyrolysis.

18. The process of claim 1 wherein said fermentation residue is dewatered to less than about 80 weight percent water prior to introduction into said thermochemical converter.

19. The process of claim 18 wherein at least a portion of the supernatant from said dewatering is recycled to said fermentation reactor.

20. The process of claim 1 wherein said organic carbonaceous feed comprises terrestrial plant material.

21. The process of claim 1 wherein said organic carbonaceous feed comprises aquatic plant material.

22. The process of claim 1 wherein said organic carbonaceous feed comprises organic waste.

23. The process of claim 1 wherein said organic carbonaceous feed comprises peat.

24. The process of claim 1 wherein said portion of thermochemical products comprises ammonia containing gas passed to said fermentation reactor.

25. The process of claim 1 wherein carbon dioxide and hydrogen from extra-process sources are added to said fermentation reactor.

26. The process of claim 1 wherein additional organic carbonaceous feed is added to said thermochemical converter, said thermochemical converter producing gaseous product comprising fuel gas, said produced fuel gas and thermal transfer from said thermochemical converter providing all overall process energy requirements.

27. The process of claim 26 wherein the overall process energy efficiency is greater than 50 percent.

28. The process of claim 26 wherein said additional organic carbonaceous feed comprises crop residues.

29. The process of claim 1 wherein over about 50 percent of said organic carbon component of said fermentation residue is thermochemically converted to gaseous or liquid thermochemical products.

30. In a process for carbonaceous liquefaction to produce alcohol containing liquid fuels, the improvement comprising beneficiation of fermenting organic carbonaceous feed under alcohol producing conditions in an active alcohol producing biological liquid culture by addition of a beneficiation agent selected from the group consisting of hydrogen, carbon dioxide and mixtures thereof.

31. The process of claim 30 wherein said beneficiation agent is hydrogen.

32. The process of claim 30 wherein said beneficiation agent is carbon dioxide.

33. The process of claim 30 wherein said beneficiation agent is a mixture of hydrogen and carbon dioxide.

* * * * *